United States Patent [19]

Suzuki

[11] Patent Number: 5,279,145
[45] Date of Patent: Jan. 18, 1994

[54] HEATER CONTROL DEVICE FOR AN AIR-FUEL RATIO SENSOR

[75] Inventor: Hiroyoshi Suzuki, Himeji, Japan
[73] Assignee: Mitsubishi Denki K.K., Tokyo, Japan
[21] Appl. No.: 965,435
[22] Filed: Oct. 23, 1992

Related U.S. Application Data

[62] Division of Ser. No. 754,853, Sep. 4, 1991.

[30] Foreign Application Priority Data

Oct. 22, 1990 [JP] Japan .................. 2-285460
Oct. 22, 1990 [JP] Japan .................. 2-285461

[51] Int. Cl.⁵ .................. G01N 27/58; G01N 27/12
[52] U.S. Cl. .................. 73/23.32; 73/23.31;
324/610; 324/611; 324/706; 324/720
[58] Field of Search ............ 374/172, 173; 324/611,
324/706, 720, 725; 73/27 R, 765, 168, 172, 173,
766, 23.31, 23.32

[56] References Cited

U.S. PATENT DOCUMENTS

| | | | |
|---|---|---|---|
| 3,117,448 | 1/1964 | Gilmont et al. | 374/168 |
| 3,201,990 | 8/1965 | Wald | 374/168 |
| 3,225,297 | 12/1965 | Burley et al. | 374/172 |
| 3,339,414 | 9/1967 | Coor | 374/168 |
| 3,913,403 | 10/1975 | Accara | 374/173 |
| 4,000,454 | 12/1976 | Brakl | 374/168 |
| 4,294,116 | 10/1981 | Yamamura et al. | 374/172 |
| 4,309,653 | 1/1982 | Stack | 374/173 |
| 4,516,865 | 5/1984 | Hideo | 374/172 |
| 4,963,246 | 10/1990 | Nakajima et al. | |
| 5,182,519 | 1/1993 | Suzuki | 324/611 |

FOREIGN PATENT DOCUMENTS

| | | | |
|---|---|---|---|
| 3936333 | 5/1990 | Fed. Rep. of Germany. | |
| 55-106328 | 8/1980 | Japan | 374/172 |
| 56-61627 | 5/1981 | Japan | 374/173 |
| 99852 | 5/1986 | Japan. | |
| 035347 | 6/1986 | Japan. | |
| 62-12873 | 1/1987 | Japan | 324/611 |
| 63-277981 | 11/1988 | Japan | 324/611 |
| 1155261 | 6/1989 | Japan. | |
| 2061545 | 3/1990 | Japan. | |

*Primary Examiner*—Kenneth A. Wieder
*Assistant Examiner*—Jose M. Solis
*Attorney, Agent, or Firm*—Sughrue, Mion, Zinn, Macpeak & Seas

[57] ABSTRACT

A heater control device for an air-fuel ratio sensor which comprises: an air-fuel ratio sensor comprising a sensor element which detects an air-fuel ratio state of exhaust gas of an engine, and a heater which heats the sensor elements; a heater current flow control means for controlling a value of a resistance of the heater to be a target resistance value; a harness having a couple of couplers at both ends thereof which connects between the air-fuel ratio sensor and the heater current flow control means; and a current detecting resistance which is incorporated in the coupler on the air-fuel ratio sensor side, or provided adjacent to said coupler on the air-fuel ratio sensor side, and which is connected to the heater in series and detects current of the heater.

1 Claim, 8 Drawing Sheets

FIGURE 1

PRIOR ART

FIGURE 8

HEATER CONTROL DEVICE FOR AN AIR-FUEL RATIO SENSOR

This application is a division of application Ser. No. 754,853, filed Sep. 4, 1991.

BACKGROUND OF THE INVENTION

This invention relates to a heater control current for an air-fuel ratio sensor which detects an air-fuel ratio of an engine.

At present, an air-fuel ratio sensor is provided at an exhaust system, to accurately control the air-fuel ratio of the sucked mixture of an internal combustion engine. The air-fuel ratio sensor detects an exhaust gas composition which is correlated to the air-fuel ratio, by which a fuel supply quantity is controlled by a feedback control.

In such air-fuel ratio sensor, a heater is provided to heat the sensor element for preventing a deterioration of characteristic of the sensor, and for removing the temperature dependency thereof. Various heater controls are proposed to maintain the sensor element at a constant value of an activation temperature or more. As for the control of this kind, as described in Japanese Unexamined Patent Publication No. 35347/1986, a heater control device is known, in which a bridge circuit including the heater as an element, and the heater is controlled by flowing current so that this bridge is balanced. Explanation will be given to this conventional example, referring to drawings.

Figure 1:
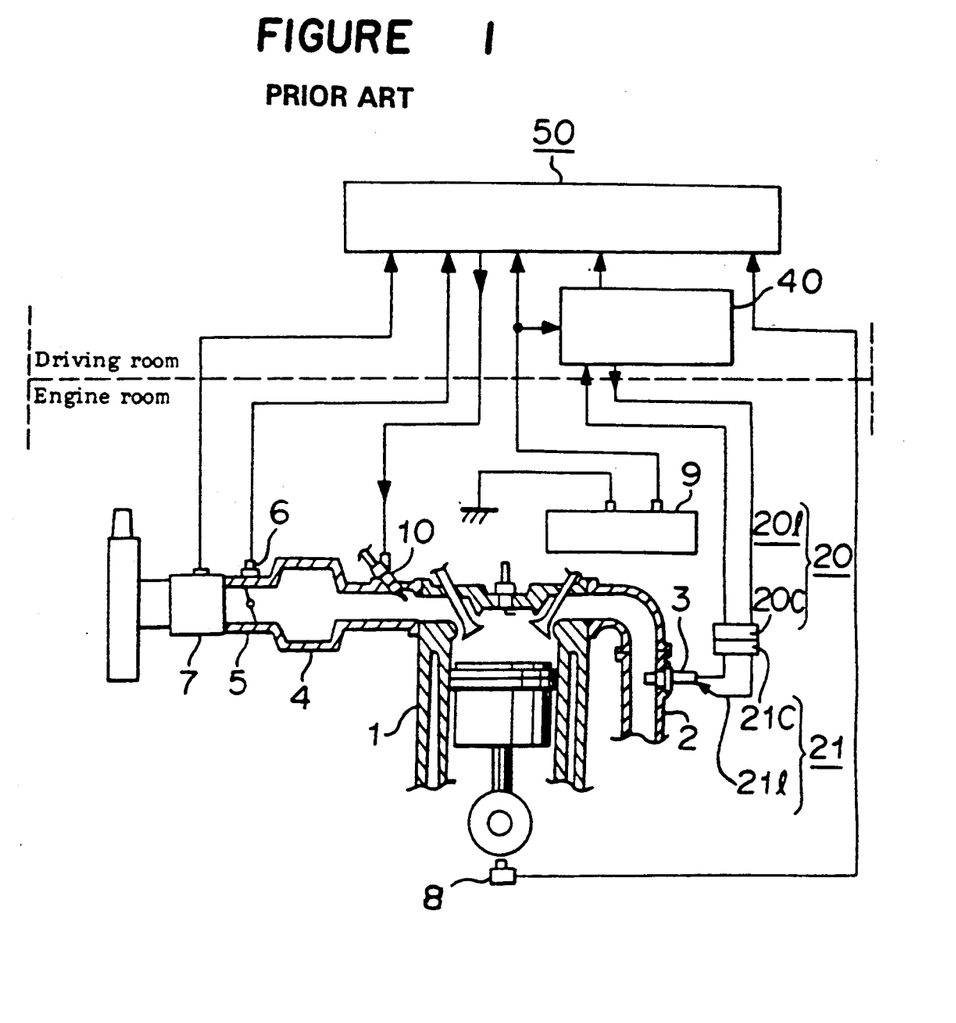
FIG. 1 is a construction diagram showing an air-fuel ratio control system to which the heater control device of the air-fuel ratio sensor is applied in the conventional and the present inventions.
Figure 2:
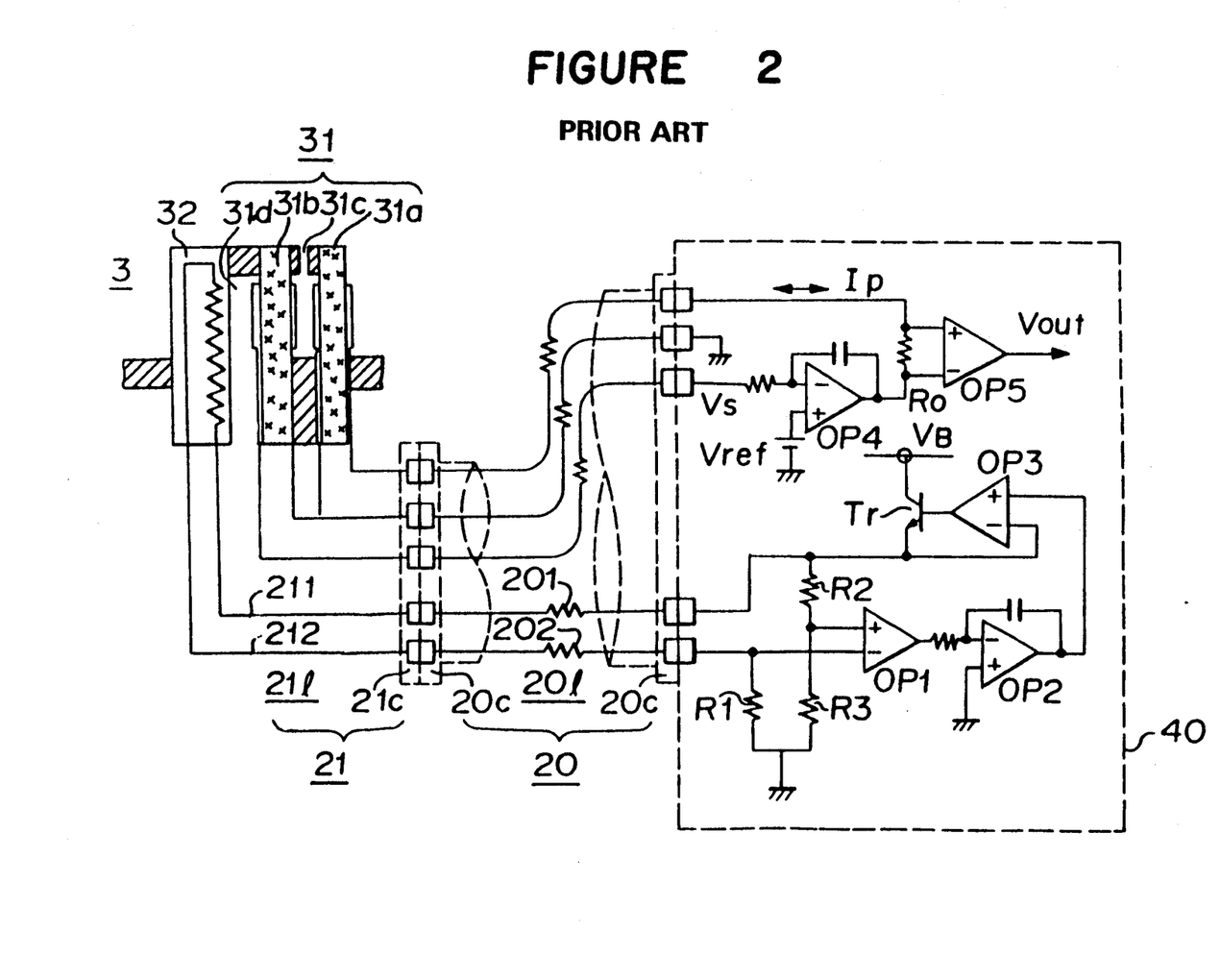
FIG. 2 is a circuit diagram showing a construction of the air fuel ratio detecting device to which the heater control device of the air-fuel ratio sensor of the conventional and the present inventions.

FIG. 1 is a total construction diagram of an air-fuel ratio control system including a heating control device of an air-fuel ratio sensor. FIG. 2 is a construction diagram of an air-fuel ratio detecting device of the sensor containing an air-fuel ratio sensor and the conventional heater control device. The air-fuel ratio control system which contains the heater control device of an air-fuel ratio sensor, shown in FIG. 1, is similar to the present invention, mentioned later. In describing the conventional heater control device of the air-fuel ratio sensor, explanation will be given by utilizing FIG. 1, and referring to FIG. 2.

In FIG. 1, a reference numeral 1 designates an engine, 2, an exhaust gas pipe, 3, an air-fuel ratio sensor installed at the exhaust gas pipe 2, 4, an intake air pipe, 5, a throttle valve, 6, a throttle position sensor of the throttle valve 5, 7, an intake air quantity sensor, 8, an engine speed sensor, 9, a battery, and 10, a fuel injection valve.

On the other hand, the air-fuel ratio sensor 3 is connected to the air-fuel ratio detecting device 40, through the harness 21 on the sensor side (lead wire 21$l$, coupler 21c), and the harness 20 on the air-fuel ratio detecting device side (lead wire 20$l$, coupler 20c ).

Furthermore, a numeral 50 designates an air-fuel ratio control device, which is installed in a driving room as well as the air-fuel ratio detecting device 40. In the drawing, the intake air quantity $Q_a$ the throttle opening degree $\theta$ and the engine revolution number $N_e$, which are the state quantities showing a running condition of the engine 1, are detected respectively, by the intake air quantity sensor 7, the throttle valve position sensor 6 and the engine speed sensor 8, and sent to the air-fuel ratio control device 50.

The air-fuel ratio the mixture of the sucked air introduced through the throttle valve 5, and fuel injected by the fuel injection valve 10 in the intake air pipe, is detected by the air-fuel ratio sensor 3 installed at the exhaust gas pipe 2, by using the air-fuel ratio detecting device 40, an output of which is sent from the air-fuel ratio detecting device 40 to the air-fuel ratio control device 50.

As shown in FIG. 2, the air-fuel ratio sensor 3 is composed of the sensor element 31 and the heater 32. The sensor element 31 is composed of the oxygen pump element 31a, the oxygen concentration cell 31b, the exhaust gas diffusion element 31c, and the standard oxygen element 31d.

The temperature of the sensor element 31 is to be maintained at a constant temperature more than an activation temperature even when exhaust gas temperature is changed by the running condition of the engine 1. For that purpose a bridge circuit is formed by the heater resistance Rh of the heater 32 and the resistances R1, R2 and R3 in the air-fuel ratio detecting device 40. In the heater control circuit including this bridge circuit, a balance voltage is detected by the differential amplifier OP1, and controlled by the integral amplifier OP2. The control result is feedback to the buffer OP3, by which the control transistor Tr is driven. The driving current flows in the path of the coupler 20c, the lead wire 201, the coupler 21c, the lead wire 211, the heater 32, the lead wire 212, the coupler 21c, the lead wire 202, the coupler 20c and the resistance R1. The driving current is controlled so that the temperature of the heat resistance R1 becomes a predetermined target value, that is, a predetermined constant temperature.

When the engine 1 is driven, the heater 32 is driven, and the temperature thereof becomes a constant temperature which is determined by the bridge circuit, and the sensor element 31 is activated, the oxygen concentration cell 31b generates an electro motive force $V_s$ which corresponds with an oxygen concentration difference of the exhaust gas diffusing element 31c and the standard oxygen element 31d.

When the electro motive force Vs is controlled by flowing the control current Ip in the oxygen pump element 31a, so that it becomes a predetermined constant voltage $V_{ref}$ through the differential integral amplifier OP4 in the air-fuel ratio detecting device 40, the control current Ip becomes proportional to the air-fuel ratio.

The control device Ip is detected by the detecting resistance $R_o$, and is amplified by the differential amplifier OP5, by which the air-fuel ratio output Vout is obtained.

The air-fuel ratio control device 50 calculates the fuel injection quantity which is compatible to the actual intake air quantity, concretely, a valve opening time of the fuel injection valve 9, based on memorized programs and data, so that a predetermined air-fuel ratio is obtained, from the information of the revolution number Ne, the intake air quantity Qa, the throttle valve opening degree $\theta$, the battery voltage VB and the like. Furthermore, the air-fuel ratio control device 50 controls the fuel injection quantity by a feedback control, by injecting fuel corresponding with the valve opening time from the fuel injection valve 10, so that the air-fuel ratio of the engine 1 becomes the target air-fuel ratio.

In this occasion, since the heater resistance is controlled constant by the heater control device, the temperature of the air-fuel ratio sensor 3 is controlled in a small range of change in spite of the change of the running condition of the engine 1.

However, the heater control device of the conventional air-fuel ratio sensor is constituted as above, the air-fuel ratio detecting device 40 including the heater control device is normally arranged in a driving room. Therefore the air-fuel ratio detecting device 40 has to be connected to the air-fuel ratio sensor 3 through the long harness 20. The influence of the lead wire resistance and the coupler contact resistance of the harness 20 on the heater control temperature is not negligible. Accordingly, in such air-fuel ratio detecting device 40, the balance condition of the bridge circuit, is, from FIG. 2, $$(Rh+2R1+4Rc)/R1=R2/R3 \qquad (1)$$

where R1 is a resistance of the lead wire 201 between the coupler 20c and the air-fuel ratio detecting device 40, and Rc, the contact resistance of the coupler. Normally the resistance of the lead wire 211 is negligible because the lead wire length is short compared with that of the lead wire 20l.

Generally the heater 32 is of a platinum resistance body. The target control resistance R1 as an operational temperature is set so that a balance condition of the bridge becomes, $$Rh/R1=R2/R3 \qquad (2)$$

Therefore the actual target resistance value of the heater becomes lower than the set value due to the resistances of the lead wire and the coupler (2R1+4Rc). Therefore the temperature of the air-fuel ratio sensor 3 is lowered by that amount.

The temperature lowering deviation due to this resistance (2R1+4Rc), becomes about 70° C., sensor resistance R1 of the lead wire 201 is about 150 mΩ since the length of the lead wire is normally about 5 m, the contact resistance of the coupler is several tens mΩ, and the temperature gradient of the heater 32 with respect to the resistance is about 150° C. Therefore, in the domain in which the exhaust temperature of the engine 1 is lower, the temperature of the air-fuel ratio sensor becomes lower than an allowance value, which worsens the exhaust gas and the drivability.

Moreover, when the temperature in the engine room is elevated, and the lead wire resistance R1 is increased, this temperature lowering tendency becomes further significant, which deteriorates the sensors.

SUMMARY OF THE INVENTION

It is an object of the present invention to solve the above problem. It is an object of the present invention to provide a heater control device of an air-fuel ratio sensor capable of restricting the lowering of the sensor temperature to a minimum even when the harness length between the air-fuel ratio sensor and the detecting circuit is set long, and which does not cause the worsening of the exhaust gas and the drivability or the deterioration of sensor.

According to an aspect of the present invention, there is provided a heater control device for an air-fuel ratio sensor which comprises: an air-fuel ratio sensor comprising a sensor element which detects an air-fuel ratio state of exhaust gas of an engine, and a heater which heats the sensor elements; a heater current flow control means for controlling value of a resistance of the heater to be a target resistance value; a harness having a couple of couplers at both ends thereof which connects between the air-fuel ratio sensor and the heater current flow control means; and a current detecting resistance which is incorporated in the coupler on the air-fuel ratio sensor side, or provided adjacent to said coupler on the air-fuel ratio sensor side, and which is connected to the heater in series and detects current of the heater.

According to another aspect of the present invention, there is provided a heater control device for an air-fuel ratio sensor which comprises: a bridge circuit comprising a first resistance which is connected to a heater of an air-fuel ratio sensor which detects an air-fuel ratio state of exhaust gas of an engine, through a harness, and which forms a series circuit with the heater, and a second and a third resistances connected in series, which are connected to the first resistance and said series circuit in parallel; a current flow control means which controls voltage or current which is supplied to the bridge circuit so that the bridge circuit is balanced; and a harness compensating resistance which is connected to the second resistance in parallel, and which compensates a resistance of the harness.

DETAILED DESCRIPTION OF THE PREFERRED EMBODIMENTS

Explanation will be given to an embodiment of the heater control device of the air-fuel ratio sensor according to the present invention, referring to the drawings. The total construction diagram showing an air-fuel ratio control system including the heater control device of the air-fuel ratio sensor according to the present invention, is the same with FIG. 1, and the air-fuel ratio sensor thereof and the air-fuel ratio detecting device thereof are the same with those in FIG. 2. However the construction of the heater control device in FIG. 3 is different with that in the conventional example.

Figure 3:
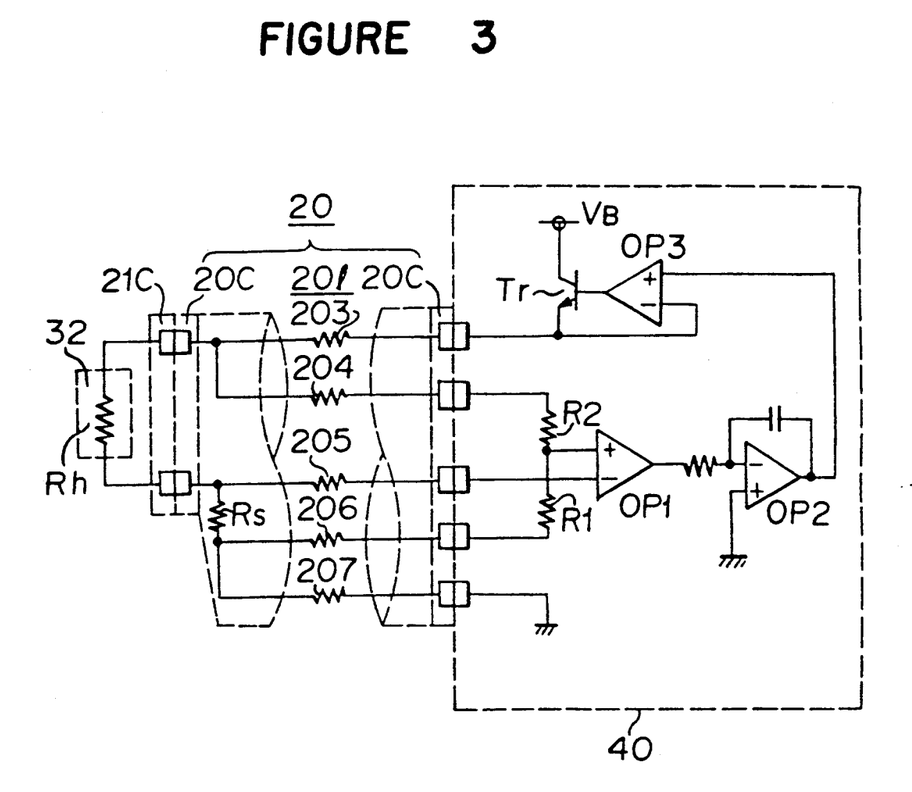
FIG. 3 is a circuit diagram showing an embodiment of the heater control device of the air-fuel ratio sensor according to the present invention.

FIG. 3 is the circuit diagram showing an embodiment of the construction of the heater control device of the air-fuel ratio sensor according to the present invention. In FIG. 3, a reference numeral 203 designates a driving lead wire which connects the control transistor Tr in the air-fuel ratio detecting device 40, to the heater 32, 204, a control lead wire which is shunted from the driving lead wire 203 at adjacent to the coupler 20c, and which is connected to the opposite resistance R2 for the bridge of the air-fuel ratio detecting device 40, 205, a control lead wire which connects the connection point of the heater 32 and the current detecting resistance Rs which is connected to the heater 32 in series and is arranged adjacent to coupler 20c, and the minus terminal of the differential amplifier OP1 in the air-fuel ratio detecting device 40, 206, a control lead wire which connects the ground side of the current detecting resistance Rs and the opposite resistance R1, and 207, the driving lead wire which connects the ground side of the current detecting resistance Rs and the ground.

Figure 4:
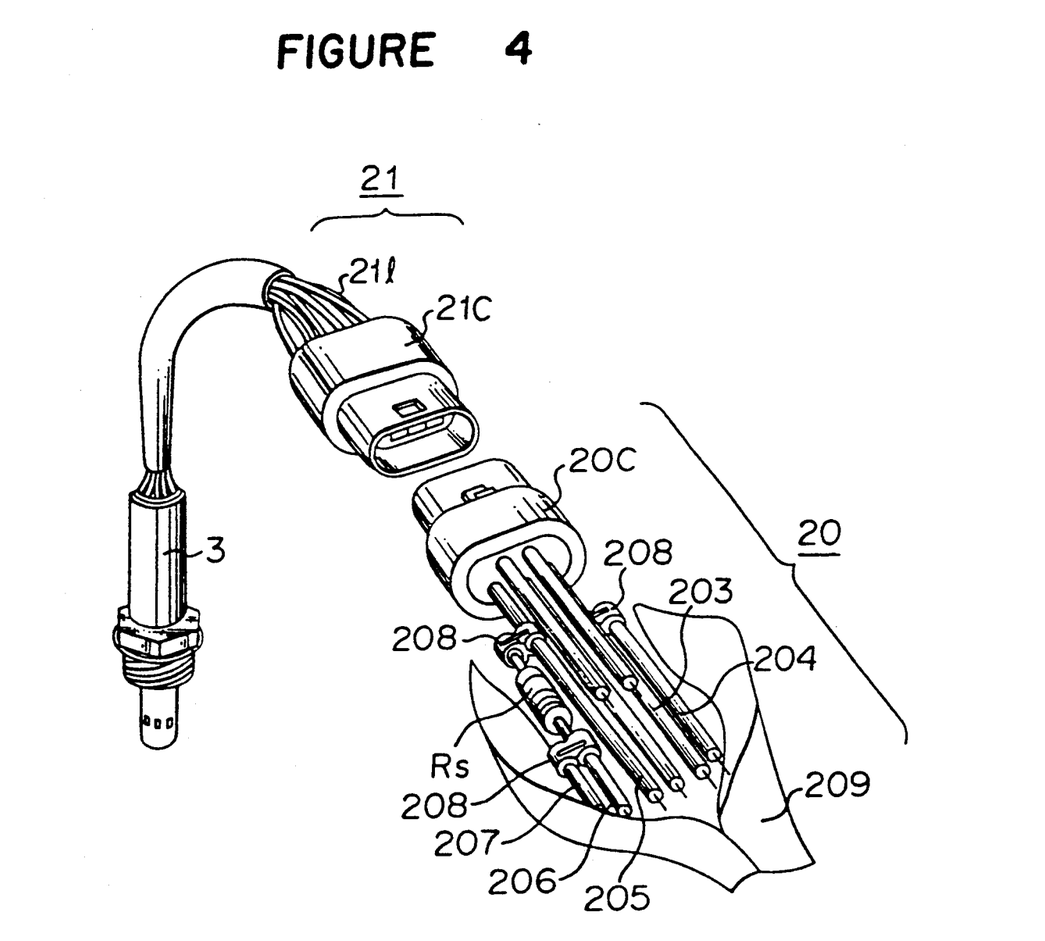
FIG. 4 is an exploded perspective showing an embodiment of a harness portion according to the present invention.

FIG. 4 is a exploded perspective showing an embodiment of the construction of the harness portion according to the present invention. The driving lead wire 203 and the control lead wire 204 are connected by the caulked connection terminal 208 at adjacent to the coupler 20c. The control lead wire 205 is similarly connected to the current detecting resistance Rs by the caulked connection terminal 208 at adjacent to the coupler 20c. The control lead wire 206 and driving lead wire 207 are similarly connected to the other end of the current detecting resistance Rs. Furthermore, the whole body constituted of these is tightly covered by the heat contraction tube 209.

Since almost no current is flown in the control lead wires 204, 205 and 206, it is possible to utilize fine wires compared with the driving lead wires. The wire diameter of the harness 20 does not becomes considerably large. The other constructions are the same with those in the conventional example. The same notations are given to the same parts with those in FIGS. 1 and 2.

Next, explanation will be give to the operation. In FIG. 3, when the driving current is flown to the bridge from the battery voltage VB through the control transistor Tr, the driving lead wire 203, and the driving lead wire 207, the potential at the connection point between opposite resistances R2 and R1 of the bridge is inputted to the plus terminal of the differential amplifier OP1, and the potential at the connection point between the heater resistance Rh and the current detecting resistance Rs is inputted to the minus terminal of the differential amplifier OP1. The error voltage is amplified by the differential amplifier OP1 and is outputted to the integrator OP2.

This integral amplifier OP2 controls the driving current by driving the control transistor Tr through the buffer OP3, so that the error voltage becomes 0, that is, the bridge is balanced.

In such construction, the driving current which flows in the bridge, is shunted from the connection point for the lead wires 203 and 204 to the respective elements of the bridge. Compared with the current which flows in the series resistance of the resistance Rh of the heater 32 and the current detecting resistance Rs (Rh+Rs), the current which flows in the opposite resistances of the bridge (R2+R1) through the control lead wires 204 and 206, is negligible since (R2+R1)>(Rh+Rs).

Furthermore, the current which is shunted to the minus terminal of the integral amplifier OP1 through the lead wire 205 is negligible since the input impedance of the differential amplifier OP1 is large.

As mentioned above, the driving current flows mainly in the heater resistance Rl and the current detecting resistance Rs through the lead wires 203 and 207, and does not flow in the control lead wires 204, 205, and 206. Furthermore, in the resistances of the control lead wires, Rc<R1≦R2. Since the balance potential detecting point is disposed at the end of the long lead wire 201, the balance condition of the bridge, is, $$(Rh+2Rc)/Rs = R2/R1 \quad (3)$$

Therefore the influence of the lead wire 201 of the long harness 20 can be removed.

Since the contact resistance Rc of the coupler is several tens mΩ as mentioned above, and the temperature lowering deviation by this contact resistance becomes about 10° C. or less in comparison with about 70° C. of the conventional device, in this embodiment, the temperature of the heater 32 can be controlled to almost the target temperature. Therefore by preventing the lowering of the temperature of the air-fuel ratio sensor due to the resistance of the harness to a minimum value, the heater control of the air-fuel ratio sensor becomes possible which does not cause the worsening of the drivability or the deterioration of the sensor.

Furthermore in this embodiment as shown in FIG. 2, a case is shown in which the current detecting resistance Rs is disposed at adjacent to the coupler 20c of the harness 20. However the current detecting resistance may be incorporated in the coupler 20c and connect to the lead wire.

Figure 5:
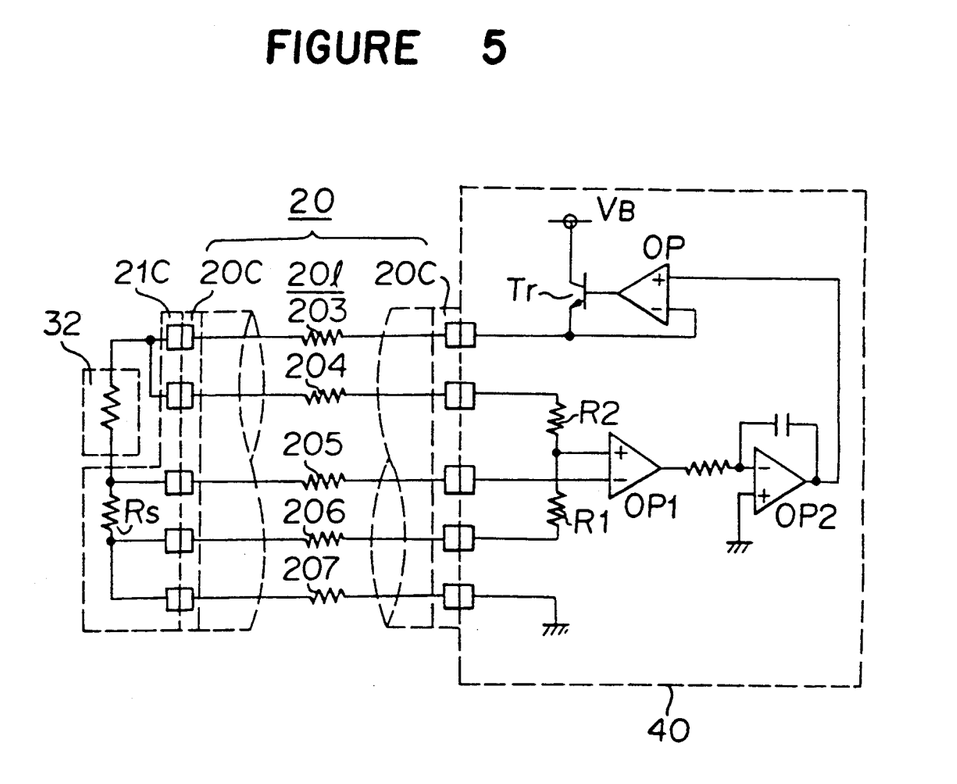
FIGS. 5 and 6 are construction diagrams respectively, of air-fuel ratio control systems to which the heater devices of the air-fuel ratio sensor are applied, according to the present invention.

FIG. 5 is a construction diagram of another embodiment of the heater control device of the air-fuel control sensor according to the present invention. The connection point of the lead wires 203 and 204 is provided in the harness 21 on the sensor side. The current detecting resistance Rs is incorporated in the coupler 21c on the sensor side, or disposed at adjacent to the coupler 21c of the harness 21 on the sensor side.

In this embodiment the balance condition of the bridge becomes the same with equation (2). Compared with the former embodiment, the number of pins of the coupler on the sensor side is increased. However, since it constitutes a complete four terminal construction, it has an effect in which influence of the resistance of the harness is completely removed.

Figure 6:
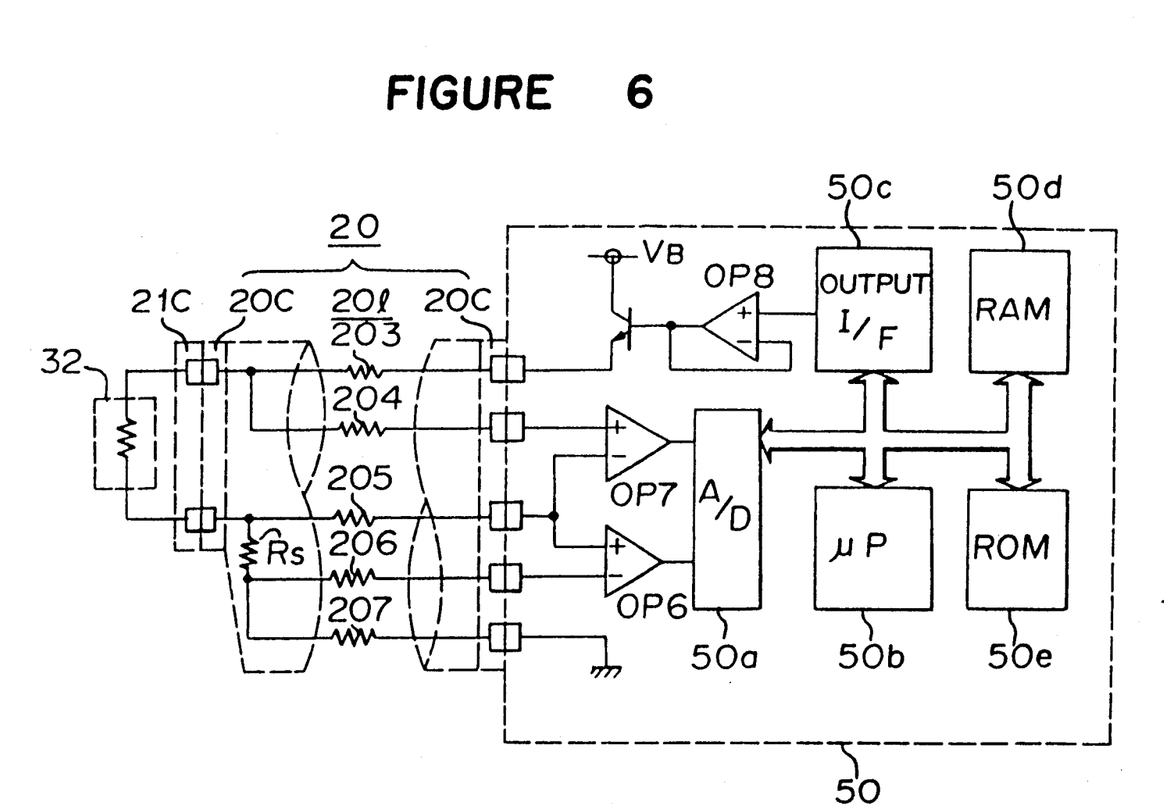

FIG. 6 is a construction diagram showing another embodiment of the heater control device of the air-fuel ratio sensor according to the present invention. The heater does not utilize a bridge. The heater resistance constant control is performed by detecting the heater voltage Vh and the heater current Ih. In the drawing, the air-fuel ratio control device 50 is utilized for the control.

The difference voltage V2 {(Rh+2Rc)×Ih} between the lead wires 204 and 205 is inputted to the differential amplifier OP7 by which the voltage Vh in the heater 32 is detected. The differential voltage V1 (Rs×Ih) between the lead wires 205 and 206 is inputted to the differential amplifier OP6, by which the electric current Ih flown in the heater 32 is detected.

The outputs of the differential amplifiers OP6 and OP7 are A/D transformed by the analog/digital (hereinafter, A/D) transformer 50a. By using the outputs of the A/D transformer 50a, (Rh+2Rc)=V2/V1×Rs is calculated. A driving signal is outputted to the output interface (hereinafter, I/F) 50c, so that the lefthand side resistance value of the equation becomes a target value, that is, V2/V1 becomes a predetermined constant value. By driving the control transistor Tr through the buffer OP8, the control is performed so that the resistance (Rh+2Rc) becomes constant.

A reference numeral 50d is a RAM which temporarily memorizes and reads out the calculation result of the microprocessor 50b or the like, and 50e, a ROM which stores the calculation program of the microprocessor 50b.

In the embodiment of FIG. 6, an effect which is comparable to the first embodiment may be obtained. The promotion of S/N ratio of control is expected since it is not necessary to detect a fine unbalanced voltage of the bridge using a long lead wire 201.

Furthermore, in the embodiment of FIG. 6, a case is shown in which the current detecting resistance Rs is disposed on the harness 20 side. However, an effect similar to that of the second embodiment may be obtained by arranging the current detecting resistance on the harness 21 side.

Figure 7:
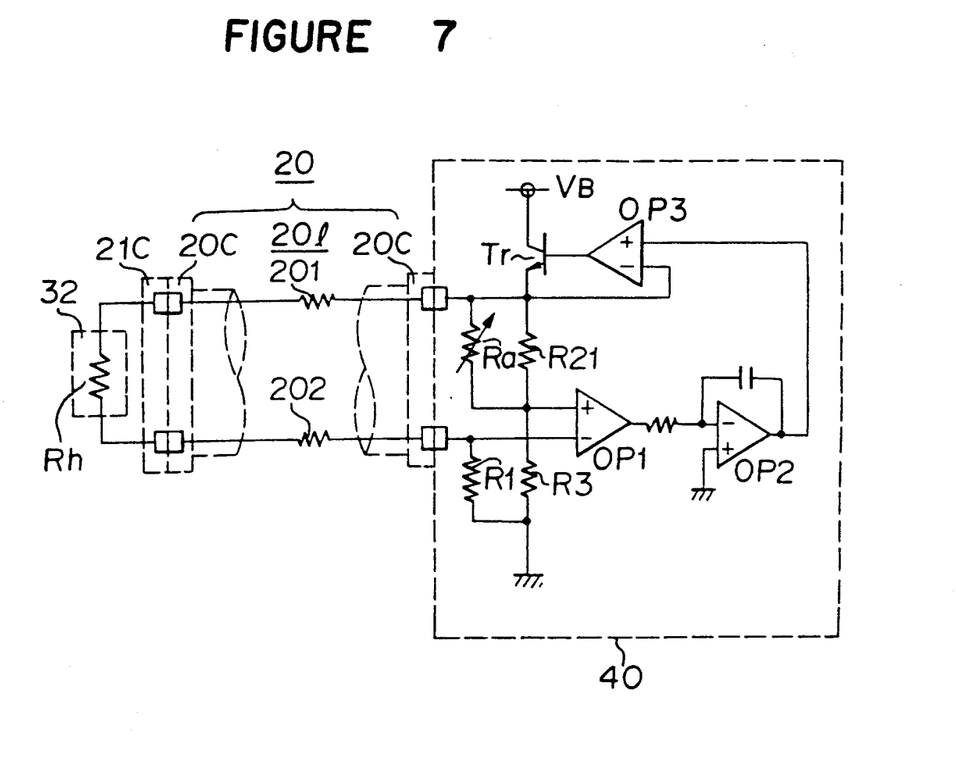
FIG. 7 is a diagram showing an embodiment of the heater control device of the air-fuel ratio sensor according to the present invention.

FIG. 7 is a construction diagram showing another embodiment of the heater control device of the air-fuel ratio sensor according to the present invention. In FIG. 7, a notation R21 designates a bridge resistance which is set larger than the resistance R2 in FIG. 2, and Ra, a harness compensation resistance, which is connected to the resistance R21 in parallel. The other constitution of the heater control device is the same with that in FIG. 4.

Next, explanation will be given to the operation of the embodiment of the present invention. In FIG. 7, when a driving current flows in the bridge from the battery voltage VB through the control transistor Tr, since the series circuit resistance (R21//Ra+R3) on the resistance R21 side is sufficiently large compared with the series circuit resistance (Rh+R1) on the heater resistance Rh side, almost all of the driving current flows in the series circuit resistance (Rh+R1) on the Rh side through the harness 20 and the harness 21.

At this occasion, the potential at the connection point between the resistance of the bridge (R21//Ra) and R3 is inputted to the plus terminal of the differential amplifier OP1, and the potential at the connection point between the heater resistance Rh and the resistance R1 is inputted to the minus terminal of the differential amplifier OP1. The error voltage amplifier at the differential amplifier OP1 is amplified. The integral amplifier OP2 controls the driving current by driving the control transistor Tr through the buffer OP3, so that the error voltage becomes 0, that is, the bridge is balanced.

In such construction, the balance condition of the bridge, assuming the target heater resistance value as Rh, $$(Rh+2R1+4Rc)/R1 = (R21//Ra)/R3 \quad (4)$$

where, $$R21 = K \times R2$$

$$Ra = K \times R2 \times (1+\Delta R/Rh)/(K-1+R/Rh) \quad (5)$$

where, $$K>1, \Delta R = 2R1+4Rc$$

Following the above equations, instead of the resistance R2 shown in FIG. 2, the bridge resistance R21 is provided which is the value of the resistance R2 multiplied by a pertinent coefficient K and of which resistance value is larger than R2. In parallel with the resistance R21, the harness compensation resistance Ra is added with the value of the harness resistance $\Delta R$, that is, calculating by putting the resistance value which is approximated to the contact resistance of the coupler Rc and the lead wire resistance R1, into equation (5), the balance condition of the bridge becomes Rh/R1 = R2/R3. The temperature lowering deviation due to the harness 20 and the harness 21 can be removed, and the heater can be controlled to the target resistance value.

As a result, the heater control of the air fuel ratio sensor becomes possible without causing the worsening of the exhaust gas or the drivability or the deterioration of the sensor.

In order to compensate the resistance increment $\Delta R$ of the heater resistance due to the harness resistance, other than increasing the resistance value of the resistance R2 as stated above, it may be considered to decrease the resistance R3, or to increase the resistance R1. However, R3>R1, so that almost no driving current is flown in the series circuit side of the bridge resistance R2. Therefore the compensation accuracy can not be obtained in a system in which R1 is increased.

Furthermore generally the consumption of the power of the heater is about 10 W at its maximum, and the target resistance value of the heater is about 10 $\Omega$. Therefore it is necessary to have the driving current of 1 A maximum for flowing in the heater. Since a ratio of the voltage effect of the heater with respect to the battery voltage of the vehicle is high, the resistance R1 in series with the heater has to be R1<Rh, as for the heater resistance Rh. Accordingly, the ratio of the resistance R3 over the resistance R2 becomes R3<R2. Therefore the compensation system in which the resistance R3 is decreased, worsens the compensation accuracy with respect to the compensation by the resistance R2. Therefore it is most pertinent to make the compensation of the resistance increment $\Delta R$ due to the harness resistance by the resistance R2.

Figure 8:
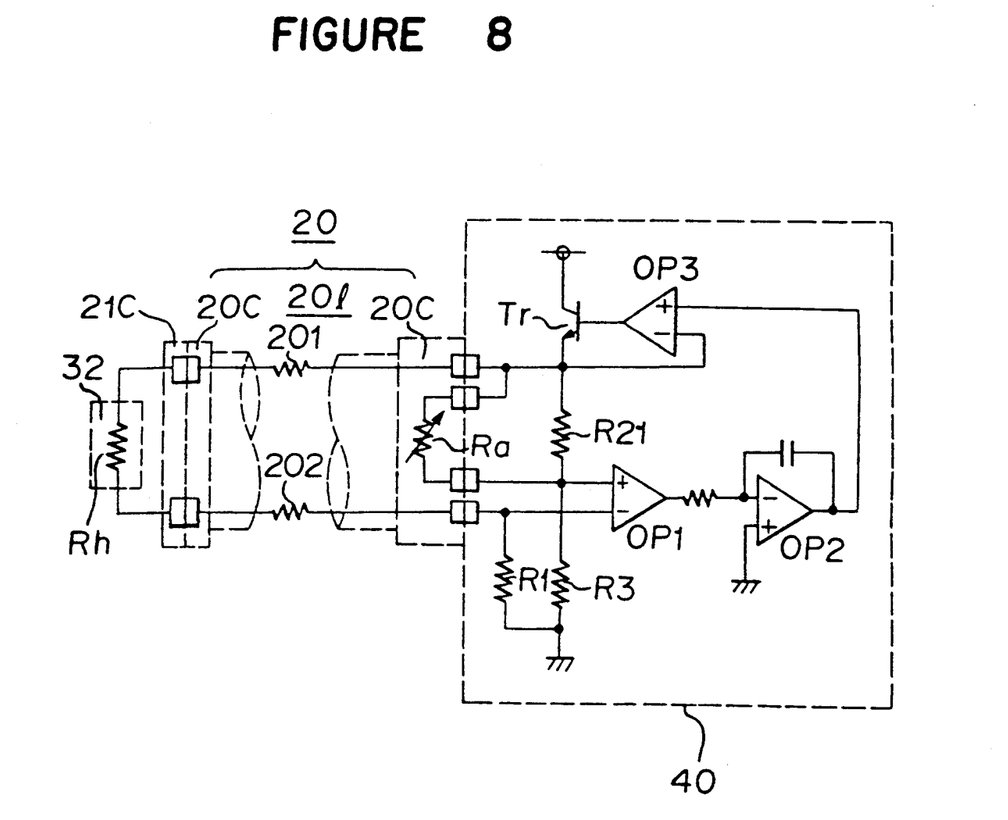
FIG. 8 is a diagram showing an embodiment of a heater control device of the air-fuel ratio sensor according to the present invention.

FIG. 8 is a construction diagram showing another embodiment of the heater control device of the air-fuel ratio sensor according to the present invention. The harness compensation resistance Ra which is connected to the resistance R21 in parallel is provided in the connector 20c on the side of the air-fuel ratio detecting device 40 in the harness 20.

Even in the above construction, the same effect as in the former embodiment can be obtained. Even in a case in which a vehicle mounted with the device is changed, and the length of the harness is changed, this embodiment has an advantage in which the compensation resistance Ra on the harness side is changed without changing the resistance value of the bridge in the air-fuel ratio detecting device 40.

Furthermore, in the above embodiment, a case is shown in which the harness compensation resistance Ra is provided in the connector 20c on the side of the air-fuel ratio detecting device 40 in the harness 20. However, the harness compensation resistance may be provided in the middle of the harness 20.

In this invention as explained as above, the current detecting resistance of the heater current flow control means which is connected to the heater of the air-fuel ratio sensor in series, is incorporated in the coupler on the air-fuel ratio sensor side of the harness which connects between the air-fuel ratio sensor and the heater flow current control means, or provided at adjacent to the coupler on the air-fuel ratio sensor side in the harness. Therefore even in the case in which the length of the harness between the air-fuel ratio sensor and the air-fuel ratio detecting device including the heater flow current control means, is set to be long, an effect can be proposed, in which the lowering of the sensor temperature is prevented to a minimum, and which does not cause the worsening of the exhaust gas or the drivability or the deterioration of the sensor.

Furthermore, in this invention, as explained above, in the heater control device of the air-fuel ratio sensor in which the air-fuel ratio sensor and the air-fuel ratio detecting device are connected by a harness, a bridge circuit comprising a first resistance which forms a series circuit with the heater, and a second and a third resistance are connected in series, which is connected to the series circuit in parallel, and the current flow control means which controls voltage for current supplied to the bridge circuit so that the bridge circuit is balanced, are provided. Furthermore a harness compensation resistance is provided in parallel with the second resistance which compensates the resistance of the harness. Therefore, even if the length of the harness is set long, the lowering of the sensor temperature is prevented to a minimum, and the invention has an effect in which a heater control device of the air fuel ratio sensor can be proposed which does not cause the worsening of the exhaust gas and the drivability or the deterioration of the sensor.

I claim:

1. A heater control device for an air-fuel ratio sensor which comprises:

an air-fuel ratio sensor comprising a sensor element which detects an air-fuel ratio state of exhaust gas of an engine, and a heater which heats the sensor elements;

a heater current flow control means for controlling current flow through the heater to maintain a predetermined constant temperature;

a harness having a plurality of couplers at both ends thereof which connects between the air-fuel ratio sensor and the heater current flow control means via connection lines, wherein said harness and said heater current flow control means are arranged such that a resistance value of said connection lines is negligible with respect to a resistance value of the heater, and wherein a total resistance of said plurality of couplers, said connection lines and the heater is substantially equivalent to said resistance value of the heater; and a current detecting resistance which is connected to the heater in series and detects current of the heater, wherein said current detecting resistance is arranged in one of two locations including a first location adjacent to said coupler on the air-fuel ratio sensor side and a second location being incorporated in the coupler on the air-fuel ratio sensor side.

* * * * *